United States Patent [19]

Kolff

[11] Patent Number: 5,722,426
[45] Date of Patent: Mar. 3, 1998

[54] CORONARY LIGHT PROBE AND METHOD OF USE

[76] Inventor: Jack Kolff, 1086 Franklin St., Johnstown, Pa. 15905

[21] Appl. No.: 607,072

[22] Filed: Feb. 26, 1996

[51] Int. Cl.$^6$ ..................................................... A61B 00/19
[52] U.S. Cl. .................. 128/898; 606/2; 607/88; 604/53
[58] Field of Search ........................ 607/88, 90; 128/664, 128/666, 667, 898, 897; 604/96, 22, 49–53, 2; 606/159, 192, 194, 2; 623/1

[56] References Cited

U.S. PATENT DOCUMENTS

| | | |
|---|---|---|
| 3,527,932 | 9/1970 | Thomas ............................ 607/90 |
| 4,961,738 | 10/1990 | Mackin . |
| 5,032,123 | 7/1991 | Katz et al. . |
| 5,061,245 | 10/1991 | Waldvogel ...................... 604/170 |
| 5,078,735 | 1/1992 | Mobin-Uddin .................... 623/1 |
| 5,167,686 | 12/1992 | Wong . |
| 5,248,311 | 9/1993 | Black et al. . |
| 5,263,952 | 11/1993 | Grace et al. . |
| 5,330,465 | 7/1994 | Doiron et al. . |
| 5,370,640 | 12/1994 | Kolff . |
| 5,411,500 | 5/1995 | Laferty et al. . |

*Primary Examiner*—Vincent Millin
*Assistant Examiner*—Kelly R. O'Hara
*Attorney, Agent, or Firm*—Thorpe, North & Western

[57] ABSTRACT

A coronary light probe and method of use are disclosed. The light probe has an elongate portion with fiber-optic cables for conveying light to a distal tip of the probe. The cables are disposed so as to laterally emit light at the distal tip so that when the probe is disposed in a vessel, the light emitted from the distal tip illuminates the vessel adjacent the distal tip. In accordance with one aspect of the present invention, the probe has a plurality of light emitting mechanisms disposed about the sides thereof proximal to the distal tip so that the light emitting mechanisms illuminate several portions of the vessel. The probe may to used to determine the location of blocking structures within a vessel, or simply to illuminate the vessel to prevent accidental laceration during surgery.

21 Claims, 3 Drawing Sheets

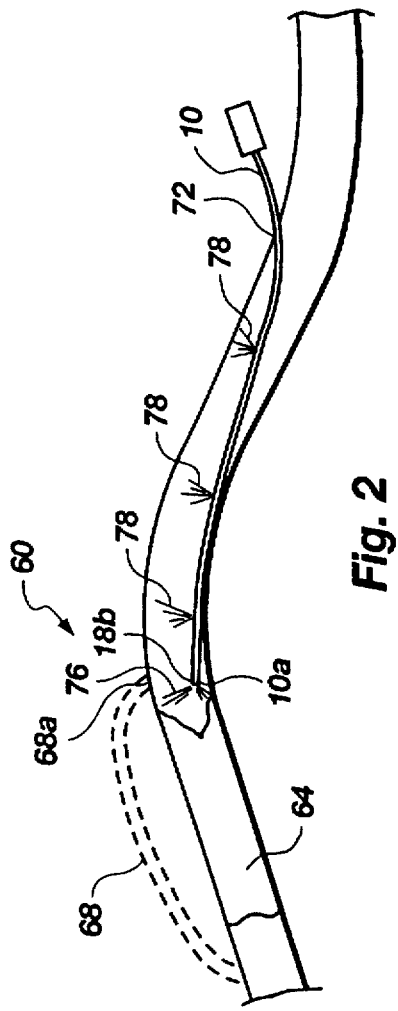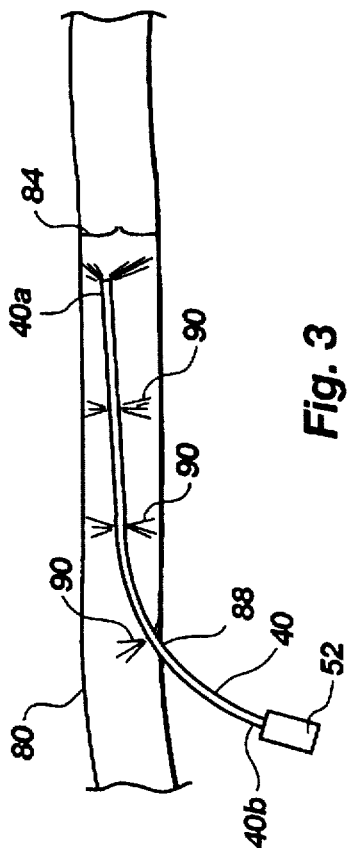

CORONARY LIGHT PROBE AND METHOD OF USE

BACKGROUND OF THE INVENTION

1. The Field of the Invention

The present invention relates to an improved apparatus and method for determining the location of arterial structures and blockages thereof during surgery so as to facilitate making incisions where necessary and to minimize the risk of accidental laceration of other arterial structures during the surgical procedure.

2. The State of the Art

There are numerous devices for use in "open heart" or "by-pass" surgery to enable the surgeon to accurately determine the location of various structures in the cardio-thoracic region and obstructions which may be disposed therein. These structures include arteries and veins, the valves disposed therein, and undesirable blockages contained within the arteries or veins, such as plaque or malfunctioning valves. For example, when performing a heart by-pass procedure, it is important that the surgeon know the exact location of the blockage which the by-pass procedure will circumvent by the addition of a by-pass vessel. If the by-pass vessel is not attached at the proper location, blood will not be properly channeled around the blockage.

To this end, a surgeon will typically form an incision in the vein, and then insert a small probe between 1 and 3 mm in thickness. The probe is advanced into the vein until its movement is stopped by the blockage which is to be by-passed by adding one or more by-pass veins which allow blood to pass out of the blocked vessel and then back into the vessel downstream from the blockage.

Once the blockage has been reached, the surgeon withdraws the probe and uses his or her fingers to mark on the probe depth at which the blockage was found. The probe is then held next to the vessel so that the surgeon can determine the exact position of the blockage before making the incision. With the position of the blockage determined, the surgeon will make an incision slightly upstream from the blockage and attach the by-pass vessel. An opposing end of the by-pass vein is attached to the vessel downstream from the blockage.

There is a need for an easier, more efficient method for determining the exact position of the blockage so as to decrease errors by the surgeon, and decrease the time necessary to complete the operation. The device used for practicing the method should be inexpensive to produce and easy to use. Ideally, such a device would illuminate not only the vessel adjacent to the blockage, but could also be used to illuminate extended portions of the vein to make them more visible during the by-pass procedure.

A probe as used to facilitate improved placement of by-pass vessels has many other cardio-thoracic applications. For example, the performance of cardio-thoracic surgeries, commonly referred to a "open heart surgery" raises numerous complications due to the close proximity of vital physiological structures which are disposed within this region. The heart is nested between the lungs, and has a myriad of veins and arteries attached thereto. As cardio-thoracic surgeries are performed, the surgeon must be ever diligent in ensuring that he or she does not accidentally lacerate one or more of the veins or arteries. While surgeons undergo years of training to avoid making such potentially deadly mistakes, the view of the veins and arteries is often at least partially obscured both by the position of other cardio-pulmonary structures, and by blood which is a natural by-product of the incision which provides access to the thoracic region.

The growth in the use of catheters to perform many functions that were previously performed by cardio-thoracic surgery has focussed attention away from the many hazards still present when operating on the heart and adjoining structures. For example, when operating on the heart, there is a significant risk that the surgeon will accidentally lacerate the coronary arteries. The coronary arteries wrap around the heart and provide blood flow to the heart. Because they lie next to the surface of the heart, the coronary arteries are often difficult to see.

If one of the coronary arteries is lacerated, the patient can quickly bleed to death. Further, because in some open-heart surgeries blood flow is often diverted to a heart/lung which mechanically pumps and oxygenates the blood, a coronary artery can be lacerated without being realized until blood flow to the heart has been returned.

Thus, it is important for surgeons to be able to determine the location of the coronary arteries so that they may be avoided. A coronary light probe which is used to illuminates portions of the coronary arteries would be particularly beneficial to surgeons during cardio-thoracic procedures. Such a device should provide sufficient illumination at one end to readily indicate to the surgeon the direction in which the probe is extending, and a plurality of lighting devices should be provided to illuminate extended portions of an artery or vein sufficiently that the surgeon does not accidentally lacerate the same.

SUMMARY OF THE INVENTION

Thus, it is an object of the present invention to provide an improved method for determining the location of vessels and blockages contained therein and increase visibility of the same.

It is another object of the present invention to provide such a method which increases the visibility of vessels adjacent a blockages within a vessel which interferes with normal blood flow through the vessel.

In is another object of the present invention to provide such a method which facilitates placement of a by-pass vessel around the blockage.

It is yet another object of the present invention to enable the surgeon to better see extended portions of the vessel on which the by-pass procedure is being performed.

It is still another object of the present invention to provide a device which can be used for increased visibility during by-pass procedures, and also for determining the location of the coronary arteries and branches thereof so as to avoid accidental laceration during invasive medical procedures on or adjacent to the heart.

The above and other objects not specifically recited are realized in specific illustrative embodiments of a coronary light probe and methods for using the same. The coronary light probe has a length of approximately four to eight inches with a light source disposed so as to emit light laterally from a distal tip of the probe. The probe is typically formed by a plurality of fine fiber-optic strands which carry the light.

In accordance with the methods of the present invention, the probe is inserted into a vessel and advanced so that the laterally emitting light at the distal tip of the probe illuminates the vessel about the probe. Thus, the illuminated vessel can be more readily seen by the surgeon. If used in a vessel with a blockage, the light emitted from the distal end of the probe indicates the location of the blockage when the probe cannot be advanced, or when the surgeon can tell the location of the blockage in the illuminated area. If used in a vessel near the specific location of the surgery, such as a coronary artery when the heart is being operated on, the illuminated portion of the vessel is more visible to surgeon and thus less likely to be lacerated.

In accordance with one aspect of the invention, the probe contains a plurality of lights spaced along lateral sides thereof. The lights illuminate small portions of the vessel in which the probe is disposed to help the surgeon follow the curvatures of the vessel and increase visibility of the vessel.

BRIEF DESCRIPTION OF THE DRAWINGS

The above and other objects, features and advantages of the invention will become apparent from a consideration of the following detailed description presented in connection with the accompanying drawings in which:

FIG. 2 shows a cross-sectional view of a blood vessel having a blockage contained therein, and the coronary probe of the present invention inserted therein for determining the location of the blockage;

FIG. 3 shows a cross-sectional view of a blood vessel having a damaged valve disposed therein, and the coronary probe of the present invention inserted in the vessel to determine the location of the valve.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
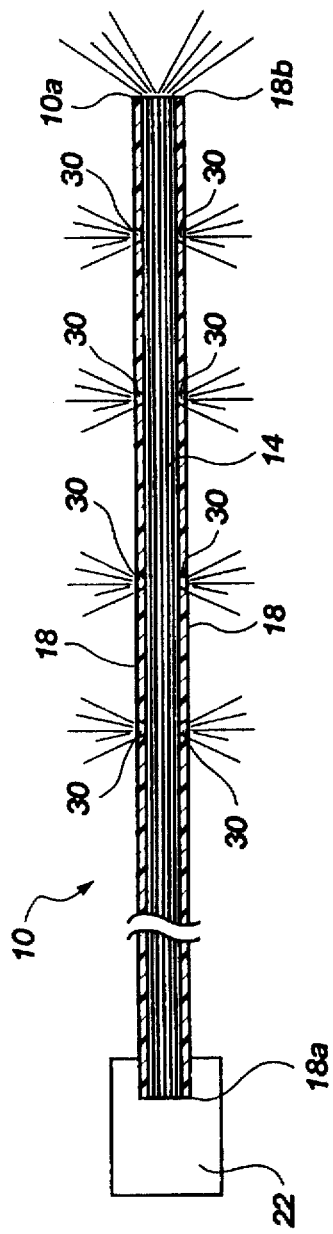
FIG. 1 shows a cross-sectional view of a coronary probe made in accordance with the principles of the present invention.

Referring now to FIG. 1, there is shown a cross-sectional view of a probe, generally indicated at 10, taken along a long axis thereof. The probe includes a plurality of fiber-optic cables 14 disposed adjacent one another. The fiber-optic cables 14 will typically be less than 0.25 mm in diameter so that a plurality of cables and a sheath 18 which surrounds the cables will have an overall diameter of about 1 mm. Of course, slightly larger or smaller sizes of the probe 10 could be made.

Disposed at a first end 18a of the sheath 18 is a light source 22. The light source emits light into the fiber-optic cables 14. The cables 14 carry the light through the sheath 18 and out an opposing second end 18b, disposed adjacent the distal tip 10a of the probe 10. The fiber-optic cables 14 are disposed to emit the light radially outwardly from the second end 18b of the sheath 18 at the distal tip 10a of the probe 10a. The light emitted radially outwardly from the distal tip 10a will be more than sufficient to illuminate a portion of the vessel, discussed in detail below.

Disposed along the sides of the sheath are a plurality of ports 30 or small holes in the sheath. Adjacent the ports 30, the fiber-optic cables 14 are scratched so that they release light out of the ports. The light emitted through the ports 30 will typically have a lower intensity than the light emitted from the distal tip 10a of the probe 10. Preferably, the light emitted from the distal tip 10a of the probe 10 will be of sufficiently greater intensity that the surgeon will be able to identify the distal tip 10a of the probe 10 within a vessel simply by the difference in intensity.

As will be appreciated by those skilled in the art, it is preferable that the probe 10 be flexible so that it can be worked through vessels without causing damage thereto. Those skilled in the art will be familiar with arrangements for the fiber-optic cables 14 which will promote such flexibility.

Figure 1A:
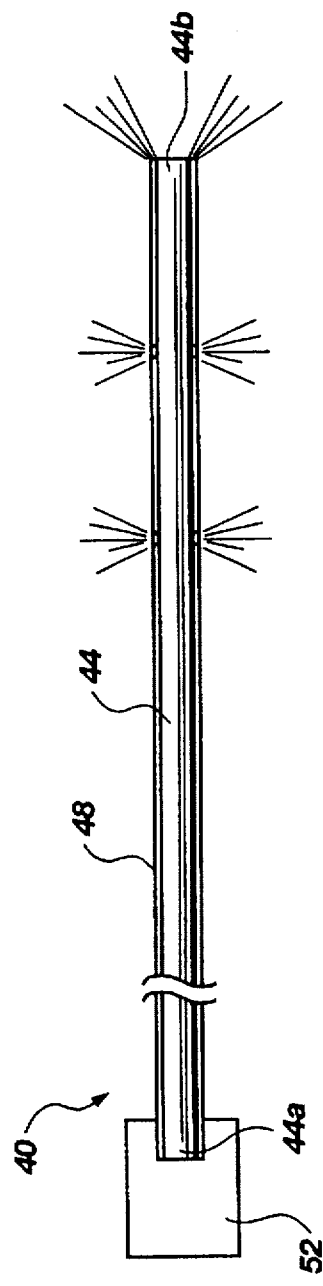
FIG. 1A shows an cross-sectional view of an alternate embodiment of the coronary probe made in accordance with the present invention.

Turning now to FIG. 1A, there is shown an alternate embodiment of a probe made in accordance with the principles of the present invention. The probe 40 includes an elongate flexible base 44 with a plurality of fiber-optic cables 48 disposed about the base. At a first end 44a of the base 44, the fiber-optic cables 48 are attached to a light source 52. At an opposing second end 44b of the base 44, the fiber-optic cables 48 terminate and are disposed to convey light laterally.

Along the length of the probe 48, the fiber-optic cables 48 can be scratched at spaced locations to cause a lesser amount of light to be emitted laterally outwardly from the probe 40 along the sides thereof. Those skilled in the art will be familiar with method for scratching the fibers to allow light to escape along the sides.

In FIG. 2, there is shown a cross-sectional view of a vessel such as an artery or vein, generally indicated at 60, with a blocking structure in the form of a plaque blockage 64 formed therein. A probe 10 as used in accordance with the principles of the present invention is also provided. The probe 10 is placed within the vessel 60 to indicate the location of the blockage 64 for the purpose of attaching a by-pass vessel 68 around the blockage.

When performing a by-pass, it is important that the surgeon know exactly where the blockage 64 is so that a by-pass vessel 68 may be properly placed around the blockage. If the by-pass vessel 68 is not properly located, the blood flow cannot circumvent the blockage and the patient is exposed to continued circulatory problems. Prior to the present invention, a surgeon wishing to know the exact location of the blockage 64 would form a small incision in the vessel 60 and push a thin metallic probe along the vessel until the probe's advancement was stopped by the blockage. The surgeon then pinched the probe between his or her fingers at the incision and withdrew the probe. The portion of the probe pinched between the surgeon's fingers was then placed next to the incision and the probe laid along the vessel 60 so that the distal tip of the probe indicated the exact location of the blockage. The surgeon could then mark the vessel 60 to indicate the location of the blockage 64 and begin making the incision for the by-pass vessel 68. The same procedure could be repeated on the other side of the blockage 64 to determine where the opposing end of the by-pass vessel 68 needed to be attached.

Those familiar with by-pass surgeries will appreciate that the prior art method is often cumbersome and difficult. This is especially true when the vessel 60 is curved, as the surgeon must hold one end of the probe adjacent the incision and conform the shape of the probe to that of the vessel. Once the distal tip is located at the blockage 64, the surgeon must mark the blockage's location. However, with two hands holding opposing ends of the probe, this can be difficult. Often, the surgeon would simply release the distal tip of the probe and use his or her fingers to mark the location until an incision could be made for attaching the by-pass vessel 68. However, should the surgeon move his or her hand, the entire procedure after the initial incision would need to be repeated.

In contrast, the present invention facilitates rapid location and marking of the blockage 64 while leaving one of the surgeon's hands free to make incisions in the vessel 60 or otherwise mark the blockage. In the present invention, a small incision 72 is made in the vessel 60 upstream or downstream a small distance from where the blockage 64 is believed to be. The distal tip 10a of the probe 10 (second end 18b of the sheath 18) is advanced through the vessel 60. Unlike the metallic probes of the prior art, the surgeon is able to closely track the exact location of the distal tip 10a of the probe 10 throughout the process by simply following the illumination of the vessel 60 provided by the light emitted from the distal tip 10a.

As the distal tip 10a approaches the blockage 64, the surgeon may be able to occasionally see where the blockage begins even through the probe has not been stopped. This may happen where the blockage has a deep, concave ending, such as is shown in FIG. 2. The thicker walls presented by the vessel/plaque combination diminish the amount of vessel illumination created by the light 76. The distal tip 10a may be advanced slightly to ensure that this is in fact the blockage 64.

However, typically the probe 10 will be advanced until its advancement is stopped by the blockage 64. Rather than needing to withdraw the probe 10 and then lay it next to the vessel 60 to determine the position of the blockage 64, the position is shown to the surgeon by the light 76 illuminating the vessel. At this point the surgeon may mark the point of the blockage 64 by holding it between two fingers or by using a marking instrument. The probe 10 may then be withdrawn from the vessel 60 and the incision for the by-pass vessel 68 made in the vessel.

In the alternative, the surgeon may use the light to mark the position of the blockage 64 within the vessel 60 and prepare the by-pass incision 68a in the vessel while the probe 10 is in place. Not only does the illumination provided by the probe 10 mark the location of the blockage 64, it also makes the vessel 60 easier for the surgeon to see as the illumination contrasts the vessel against the other vessels and blood disposed thereabout.

After the by-pass incision 68a is made, the probe 10 is withdrawn and the incision 72 is closed. The same procedure may then be repeated on the other side of the blockage to connect the opposing end of the by-pass vessel 68 and thereby complete the circumvention of the blockage 64 obstructing blood flow through the vessel 60.

Also shown in FIG. 2 are a plurality of side lights 78 formed by the ports 30 discussed with respect to FIG. 1. The side lights help to illuminate portions of the vessel 60 between the incision 72 and the portion of the vessel illuminated by the distal tip 10a of the probe 10. Because emission of light 78 along the sides of the probe 10 is of a lesser intensity than the light 76 emitted from the distal tip 10a, the surgeon is able to distinguish the distal tip 10a. However, the light 78 emitted from the sides of the probe 10 is sufficient to help the surgeon track the vessel 60 even when it is disposed in a hard to see portion of the cardiothoracic cavity.

Referring now to FIG. 3, there is shown an alternate use present invention. (While the different embodiments of the probe are used with respect to different procedures, it is to be understood that either embodiment may be used with any of the procedures discussed herein). A vessel 80 is shown in cross-section with a blocking structure in the form of a valve 84 disposed in the vessel. In the present situation, the valve 84 is damaged and must be repaired or replaced. However, before the valve can be repaired or replaced, it must be accurately located. This procedure can be done by using the probes of the prior art. However, using the probe discussed above in accordance with the principles of the present invention allows the surgeon to more quickly locate and mark the position of the valve 84 so that it can be repaired or replaced.

As with the blockage 64, the valve 84 is located by forming a small incision 88 in the vessel 80. The incision will typically be about 2 mm in length. The probe 40 is inserted through the incision 88 and is advanced until it contacts the valve 84. The surgeon may then either leave the probe 40 in place while he or she makes an incision, or may mark the location of the valve 84 in some other manner and withdraw the probe. With the location of the valve 84 properly determined, considerable time and energy may be saved.

Also shown in FIG. 3 is light 90 being emitted from the side of the probe 40 at three locations between the light emitted from the distal tip 40a of the probe 40, and the light source 52 at the opposing end 40b of the probe 40. The spaced light 90 helps the surgeon to track the vein between the bright illumination provided at the distal tip 40a and the incision 88, both of which are easy to find.

Figure 4:
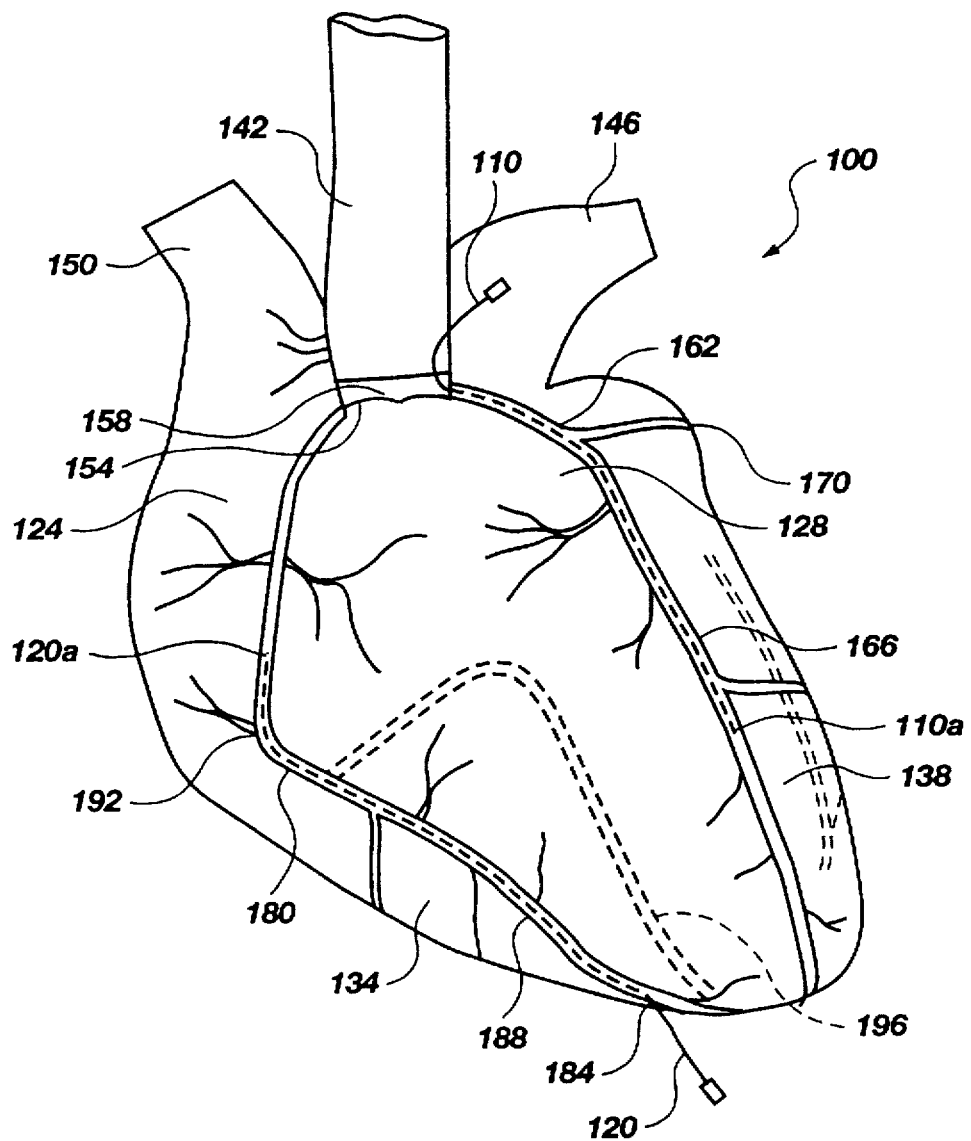
FIG. 4 shows a front view of a human heart with a plurality of probes disposed therein in accordance with the principles of the present invention.

Referring to FIG. 4, there is shown a front view of a human heart, generally indicated at 100, with two probes, generally indicated at 110 and 120, each being disposed therein in accordance with the method of the present invention. The heart consists of the right and left atriums, indicated at 124 and 128, respectively. Disposed below the right and left atriums 124 and 128 are the right and left ventricles, 134 and 138 respectively.

Extending upwardly from the heart 100 is the ascending aorta 142. The pulmonary artery 146 is to the right, while the superior vena cava 150 is to the left. In accordance with one aspect of the invention, a probe, such as probe 110 is advanced down one of the coronary arteries to make the artery easier to see during open heart surgery and to prevent accidental laceration of the artery which, if undiscovered could seriously harm, if not kill, the patient.

Probe 110 is placed in the left coronary artery 162 by making a small incision in the ascending aorta adjacent the semilunar valve 154. The probe 110 passes adjacent to the aortic sinus 158 and into the left coronary artery 162. The probe 110 will typically be passed down through the left main artery, the anterior interventricular branch 166, until the distal tip is disposed sufficiently deep that the probe illuminates the portions of the artery of concern to the surgeon. Once the probe 110 is in position, the light which is emitted laterally from the probe assists the surgeon in avoiding that portion of the coronary artery during surgery. Of course, the flexible probe 110 could be turned down one of the many tributaries, such as the circumflex branch 170, if the surgeon is will be operating in that area. When placing the probe 110, the brighter light emitted from the distal tip 110a helps the surgeon to ensure that the probe is being properly inserted in the desired branch. Without the light, the surgeon would have to rely on feel to ensure that the probe was properly positioned.

Also shown in FIG. 4 is the probe 120 which is disposed in the right coronary artery 180. The probe 120 is positioned in the artery 180 by making a small incision in the distal end of the artery. As shown in FIG. 4, the incision 184 is made in the marginal branch 188 and the probe 120 is advanced to that the distal tip 120a has been turned up the main branch 192. Those skilled in the art will appreciate that the incision could have been made in the posterior interventricular branch 196 and advanced proximally up the main branch 192. Of course, incisions could be made at the proximal end of the right or left artery and the probe advanced distally as well.

Regardless of where the incision is made, the surgeon is provided with improved visibility of the artery or a branch thereof. The improved visibility is provided both by emitting light from the distal tip 110a of the probe 110 and from the light emitted along the sides.

Thus there is disclosed an improved coronary light probe and method of use. Those skilled in the art will appreciate numerous modifications which can be made without departing from the scope and spirit of the present invention. The appended claims are intended to cover such modifications.

What is claimed is:

1. A method for using a light probe in open heart/by-pass surgery to indicate the location of a blockage contained within an artery/vein and inhibiting blood flow through the artery/vein, the method comprising:

(a) selecting a probe having a lighting means disposed at a distal tip thereof for laterally emitting light;

(b) making an incision in an artery/vein for insertion of the probe;

(c) inserting the probe into the artery/vein and advancing the probe until the probe is disposed adjacent the blockage contained within the artery/vein;

(d) illuminating the artery/vein adjacent to the blockage to thereby indicate the position of the blockage;

(e) marking the artery/vein at the location of the lighting means within the artery/vein to thereby indicate a desired location for attachment of a by-pass vessel.

2. The method of claim 1, wherein step (a) comprises, more specifically, selecting a probe having a plurality of light emitting ports disposed along lateral sides thereof.

3. The method of claim 2, further comprising selecting a probe with a plurality of light emitting ports spaced along sides of the probe and disposing the probe in the artery/vein to thereby illuminate the artery/vein and facilitate enhanced visibility of the artery/vein during at least a portion of the open heart/by-pass surgery.

4. The method of claim 1, wherein step (b) comprises, more specifically, making the incision upstream from the blockage.

5. The method of claim 1, wherein step (b) comprises, more specifically, making the incision downstream from the blockage.

6. The method of claim 1, wherein step (c) comprises, more specifically, advancing the probe until the distal tip thereof contacts the blockage.

7. The method of claim 1, wherein marking the artery/vein comprises making an incision for attaching a by-pass vessel adjacent to the blockage.

8. The method of claim 1, wherein marking the artery/vein comprises leaving the distal tip adjacent the blockage and emitting light from the distal tip.

9. The method of claim 1, wherein the blockage comprises a malfunctioning valve, and wherein marking the artery/vein comprises making an incision for exposing the valve.

10. A method for facilitating placement of a by-pass vessel around a blockage contained within in a primary vessel carrying blood to thereby facilitate improved blood flow through the primary vessel, the method comprising:

(a) inserting a probe having a light emitting mechanism disposed at a distal end thereof into the primary vessel for laterally emitting light into the primary vessel; and (b) advancing the distal end of the probe in the primary vessel until the distal end is disposed adjacent the blockage; and (c) illuminating a portion of the primary vessel adjacent the blockage so as to indicate the location of the blockage which will be by-passed by the by-pass vessel.

11. The method of claim 10, wherein step (a) comprises, more specifically, making an incision in the primary vessel and inserting the probe through the incision.

12. The method of claim 10, wherein the method further comprises making an incision in the illuminated portion of the primary vessel.

13. The method of claim 10, wherein the method further comprises attaching a by-pass vessel to the portion of the primary vessel illuminated by the probe.

14. The method of claim 10, wherein step (a) comprises, more specifically, inserting a probe having a light emitting mechanism at the distal end and a plurality of light emitting mechanisms disposed about the probe proximal to the distal end to thereby illuminate portions of the primary vessel not immediately adjacent to the blockage.

15. A method for enhancing the visibility of a coronary artery during invasive surgery on one or more structures adjacent to, but not including, the coronary artery to thereby avoid accidental laceration of the coronary artery during the surgery on the one or more structures, the method comprising:

(a) providing a probe having a plurality of lighting mechanisms disposed thereon for providing light radially outwardly from the probe;

(b) sliding the probe into the coronary artery; and (c) illuminating at least two portions of the coronary artery with the lighting mechanisms disposed on the probe so as to enhance visibility of the coronary artery and thereby prevent accidental laceration of the coronary artery during surgery on the one or more structures adjacent the coronary artery.

16. The method for enhancing the visibility of a coronary artery of claim 15, wherein step (a) comprises, more specifically, using a probe having a first lighting mechanism disposed at a distal tip of the probe and a plurality of second lighting mechanisms positioned along the sides of the probe, the first lighting mechanism being sufficiently brighter than the second lighting mechanisms to facilitate visual determination by the user of the distal end of the probe within the coronary artery; and wherein step (b) comprises, more specifically, repeatedly observing the portion of the coronary artery illuminated by the first lighting mechanism to ensure that the probe is properly positioned in the coronary artery.

17. The method for enhancing the visibility of a coronary artery of claim 15, wherein the method comprises, more specifically using a probe with a plurality of lighting mechanisms spaced along the probe to illuminate an elongate portion of the coronary artery.

18. The method for enhancing the visibility of a coronary artery of claim 17, wherein the coronary artery has a main portion and a tributary portion extending from the main portion, and wherein step (b) comprises, positioning the probe within the artery so as to illuminate the main portion and a beginning of the tributary portion whereat the tributary portion joins the main portion.

19. The method for enhancing the visibility of a coronary artery of claim 15, wherein step (b) comprises, more specifically, inserting the probe into a distal (downstream) portion of the coronary artery, and advancing the probe toward a proximal (upstream) portion of the coronary artery.

20. The method for enhancing the visibility of a coronary artery of claim 19, wherein step (b) further comprises forming an incision in the distal (downstream) portion of the coronary artery for insertion of the probe into the coronary artery.

21. The method for enhancing the visibility of a coronary artery of claim 15, wherein step (b) comprises, more specifically, inserting the probe into a proximal (upstream) portion of the coronary artery, and advancing the probe toward a distal (downstream) portion of the coronary artery.

* * * * *